Figure 7:
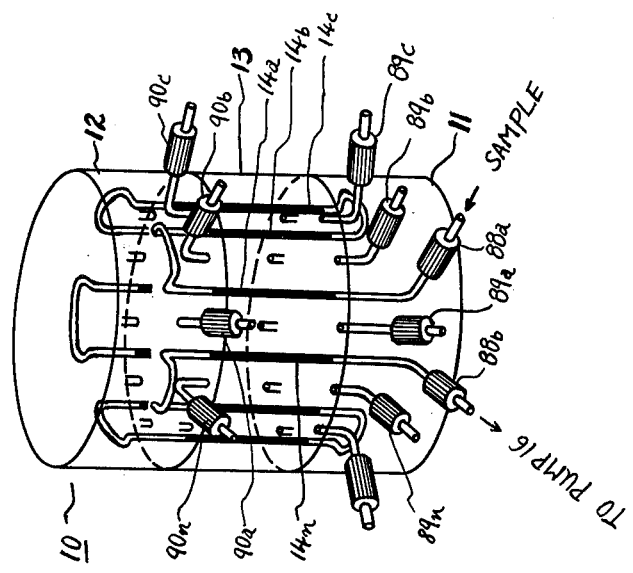

United States Patent [19]

Naono

[11] 4,090,848
[45] May 23, 1978

[54] AUTOMATIC ANALYZING APPARATUS

[75] Inventor: Toyohiko Naono, Tokyo, Japan

[73] Assignee: Nihon Denshi Kabushiki Kaisha, Tokyo, Japan

[21] Appl. No.: 666,921

[22] Filed: Mar. 15, 1976

[30] Foreign Application Priority Data

Mar. 20, 1975 Japan .................. 50-33683

[51] Int. Cl.² .............. G01N 33/16; G01N 1/14
[52] U.S. Cl. ................ 23/253 R; 23/259; 356/246
[58] Field of Search ........... 23/253 R, 230 B, 259; 356/246

[56] References Cited

U.S. PATENT DOCUMENTS

| | | | |
|---|---|---|---|
| 3,762,879 | 10/1973 | Moran | 23/253 X |
| 3,764,268 | 10/1973 | Kosowsky | 23/253 X |
| 3,799,744 | 3/1974 | Jones | 23/253 R |
| 3,841,834 | 10/1974 | Gandhi et al. | 23/253 X |
| 3,874,850 | 4/1975 | Sorensen et al. | 23/253 X |
| 3,881,872 | 5/1975 | Naono | 23/253 R |
| 3,883,305 | 5/1975 | Hoskins et al. | 23/253 R |
| 3,912,452 | 10/1975 | Sodickson et al. | 23/253 X |
| 3,932,131 | 1/1976 | Rolfo-Fontana | 23/253 X |
| 3,953,136 | 4/1976 | Hach | 23/253 X |

Primary Examiner—R.E. Serwin
Attorney, Agent, or Firm—Webb, Burden, Robinson & Webb

[57] ABSTRACT

An automatic analyzing apparatus comprising a rotatable reaction device, a plurality of reaction tubes, said reaction device stepwise rotated by a driving means whereby a reaction tube is advanced through a plurality of functional positions, that is, at the initial position of the rotatable reaction device a liquid sample is supplied to a reaction tube together with a first reagent, at the second position the sample and first reagent are stirred, at the third position a second reagent is supplied to said reaction tube, at the fourth position the sample, and first and second reagents are stirred, at the fifth position, the stirred mixture is optically measured, at the sixth position the optically measured mixture is drained off, and at the seventh position the empty reaction tube is washed and rinsed before being returned to the original position where the next liquid sample is supplied.

9 Claims, 7 Drawing Figures

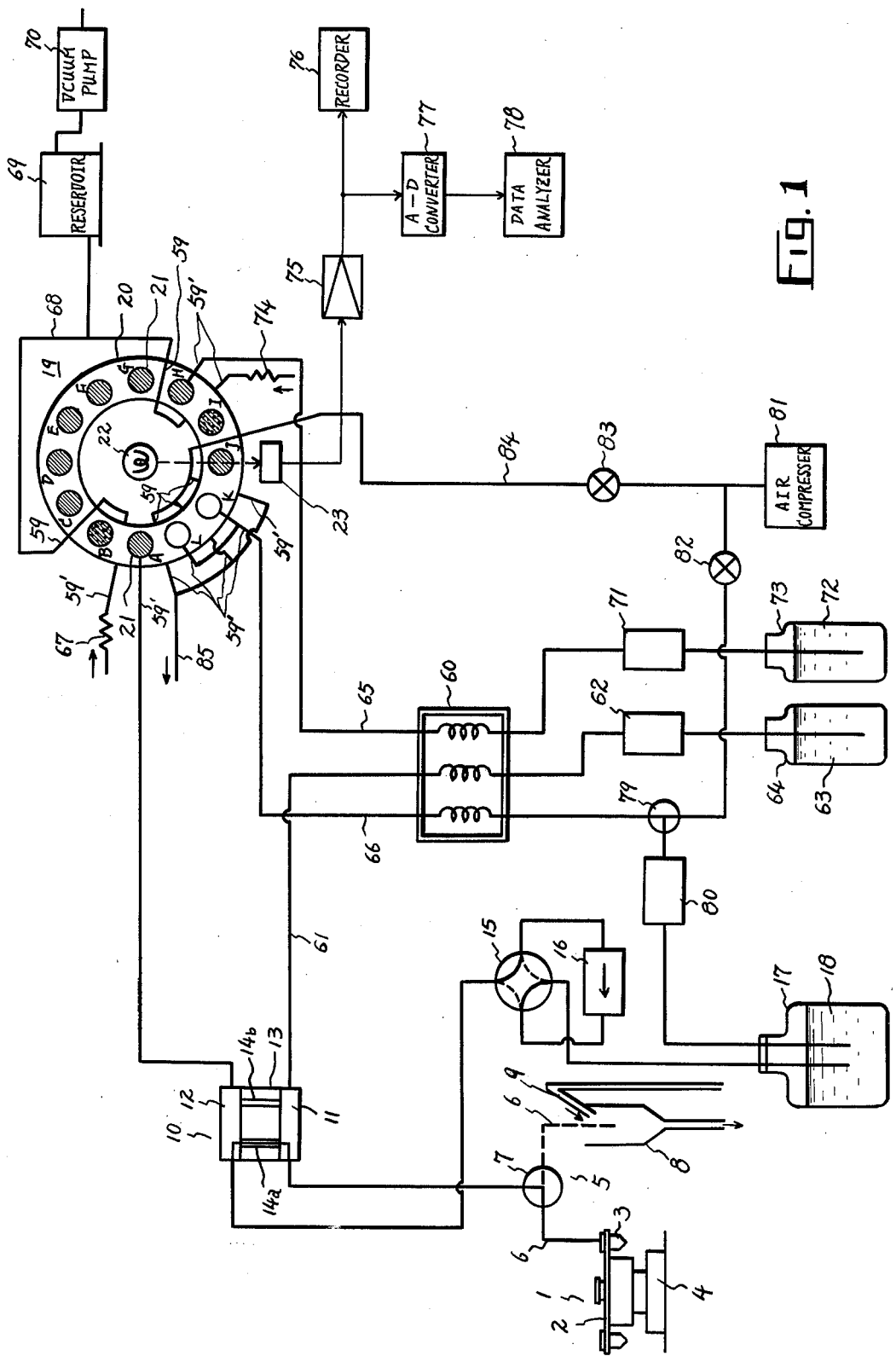

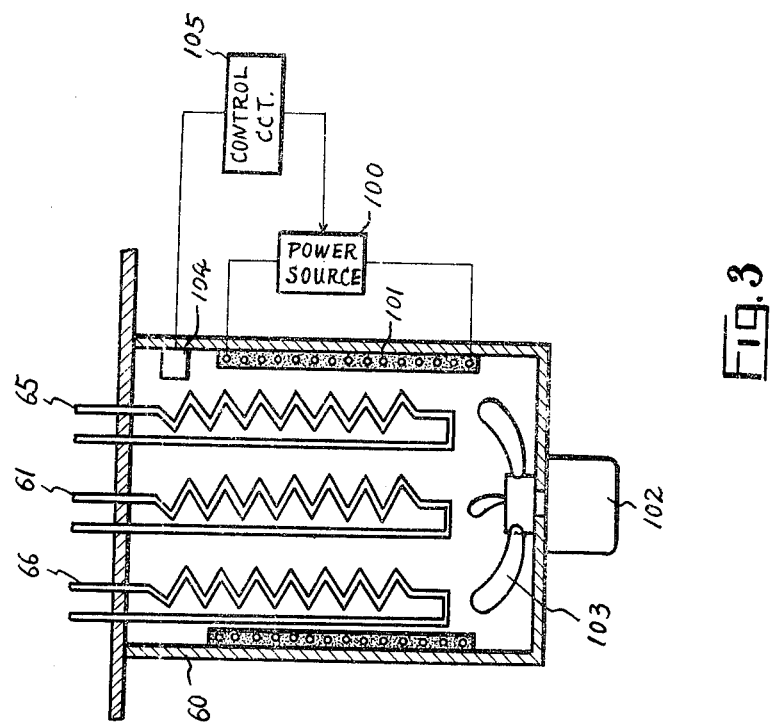
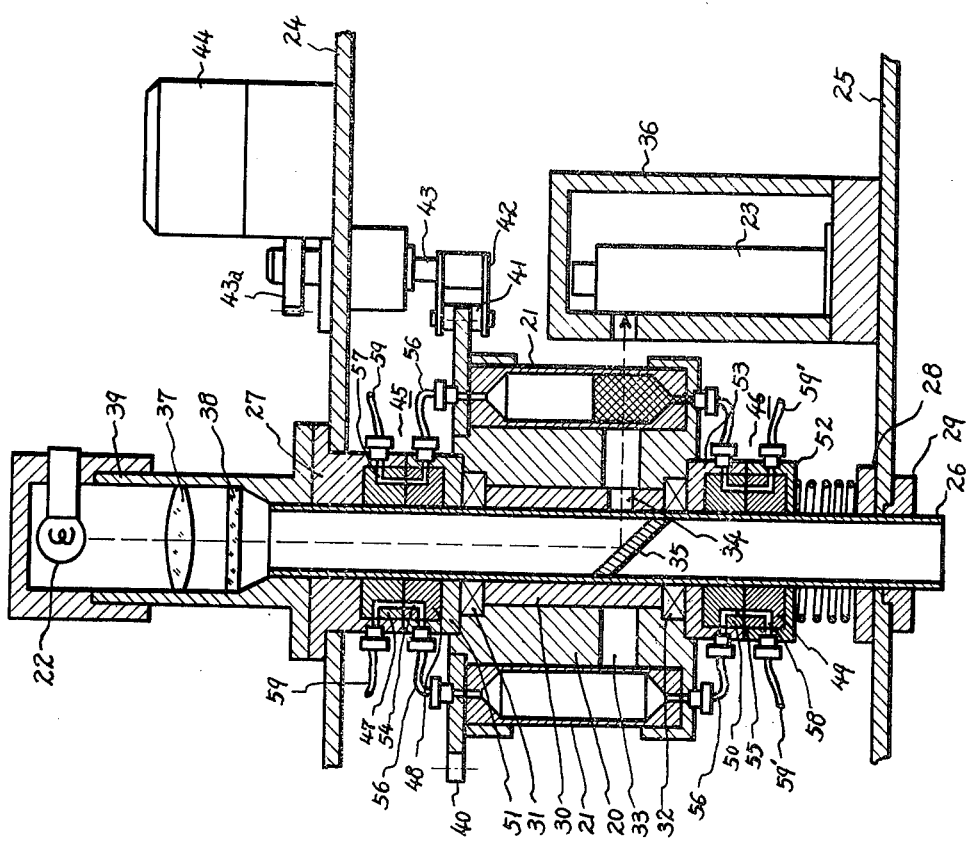
Fig. 3
Fig. 2

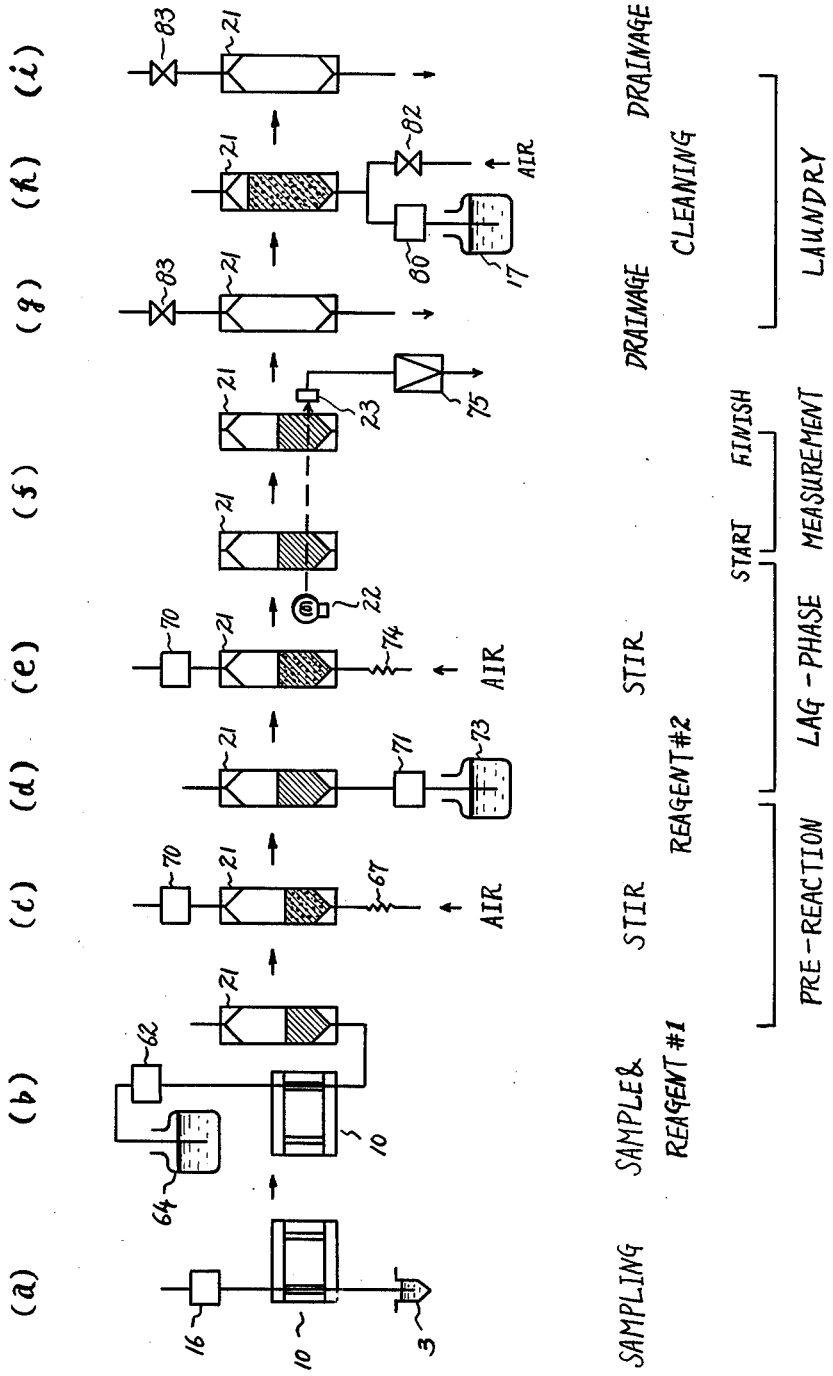

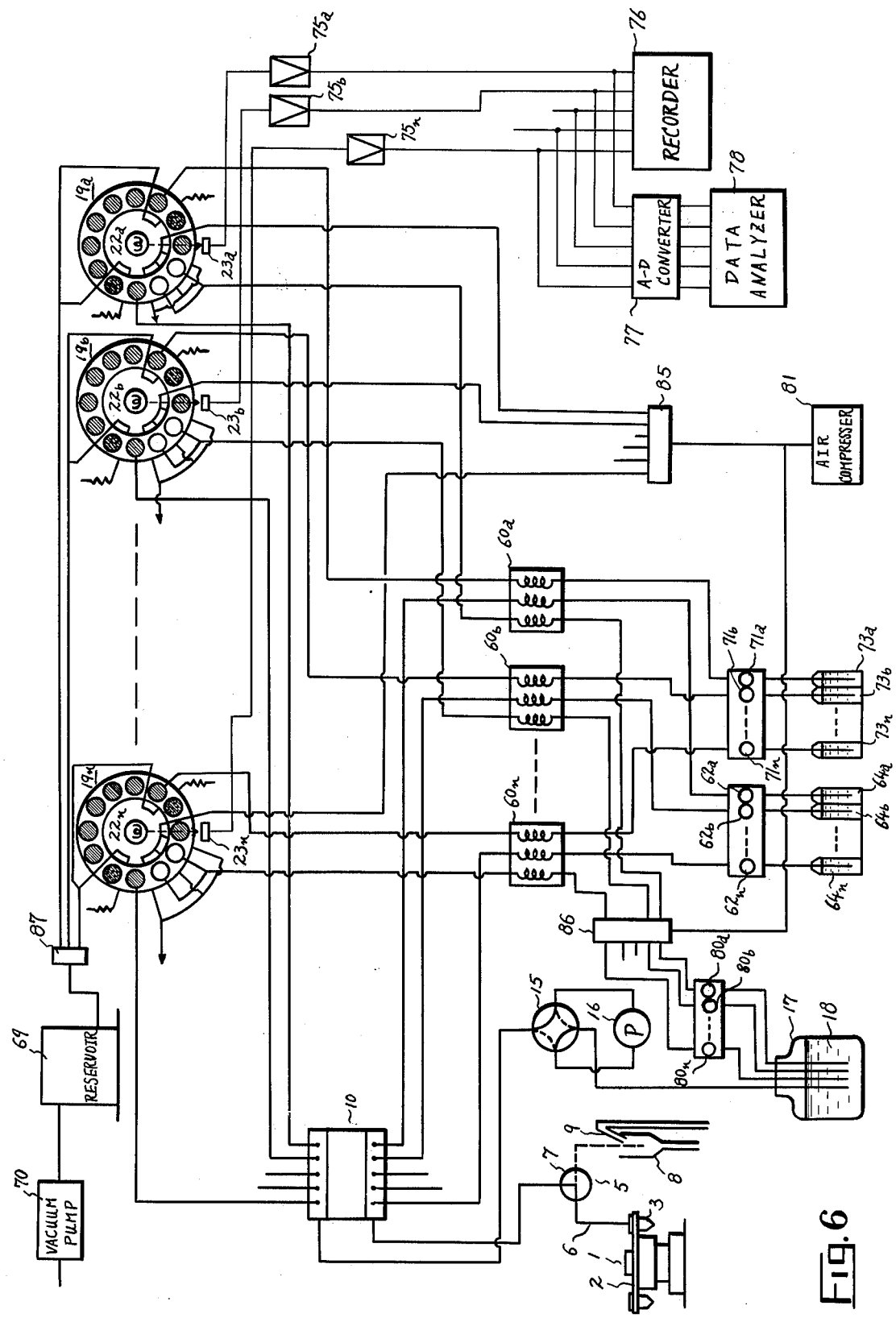

AUTOMATIC ANALYZING APPARATUS

This invention relates to an apparatus capable of automatically and sequentially analyzing blood, urine and other samples and measuring the activated value of enzymes.

Recently, in the fields of medicine, chemistry, pharmacology, there has been a growing demand for an apparatus capable of speedily and accurately analyzing liquid samples, for example, serum or urine. However, due to the various inherent problems involved, a satisfactory apparatus has not, thus far, been forthcoming.

On the other hand, subsequent to the recommendations of the International Union of Biochemistry to the effect that enzyme quantification should be carried out according the initial reaction rate, the Reaction Rate Assay medico-chemical analytical method has gained recognition as a valid and effective technique. As is well know, the enzyme reaction increases as the substrate concentration increases but ceases to increase over a certain range of concentration known as the plateau domain. By further increasing the substrate concentration beyond a certain level, the enzyme reaction rate starts to decrease. Such being the case, the reaction rate assay utilizes the palteau domain to carry out enzyme reaction and the reaction rate is measured in order to obtain the activated value of the enzyme.

However, an apparatus capable of continuously and precisely carrying out such measurements has, up to now, not been developed.

One object of this invention is to provide an apparatus capable of chemically analyzing liquid samples both speedily and precisely.

Another object of this invention is to provide an apparatus capable of simultaneously conducting a plurality of tests pertaining to the same sample.

A further object of this invention is to provide an apparatus capable of measuring the activated value of enzymes precisely, automatically and continuously.

Figure 4:
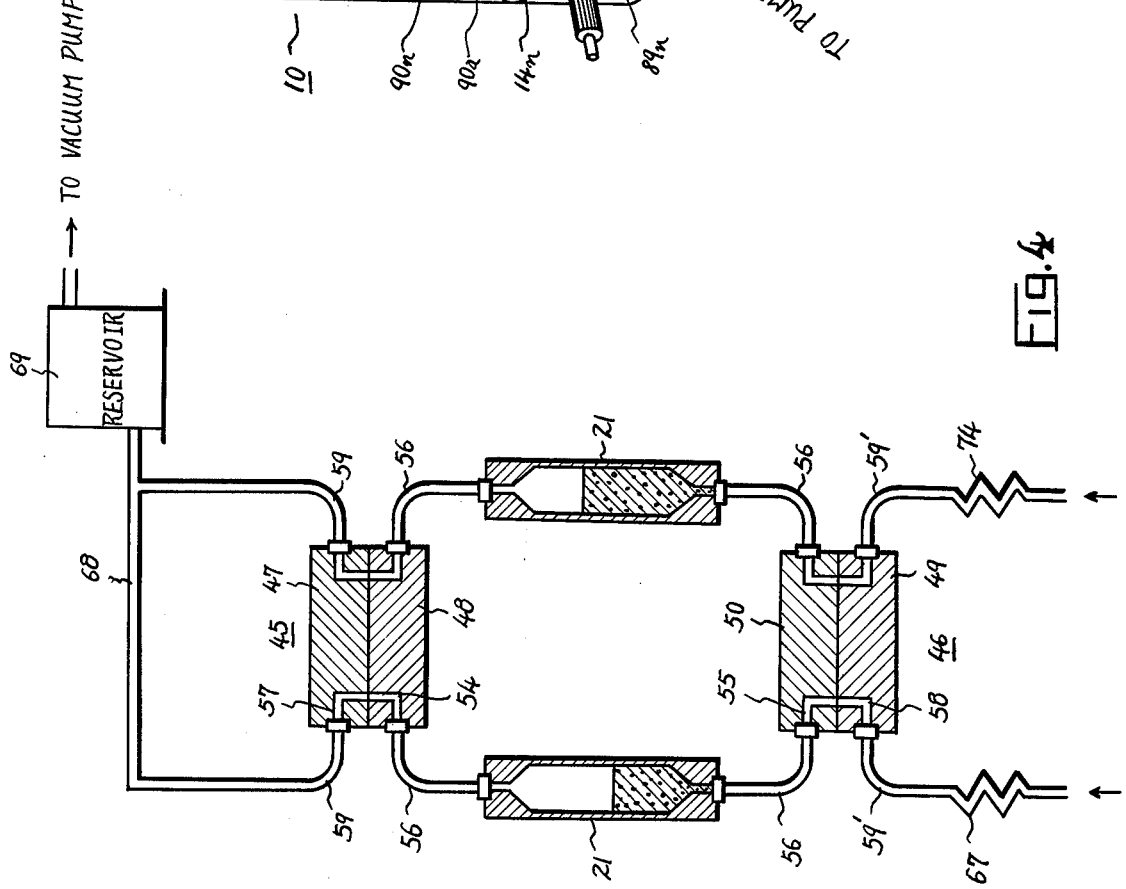

The advantages and merits of this invention will become more readily apparent by reading the following detailed description in conjunction with the accompanying drawings of which:

FIG. 1 schematically illustrates one embodiment of this invention,

FIG. 2 shows a cross-sectional view of the reaction device according to this invention, FIG. 3 shows the preheating chamber and associated circuits, FIG. 4 shows the structure of the mechanism for stirring the sample and reagent, FIG. 5 shows the step by step operational sequence of the automatic analyzing apparatus from sampling through to the final draining of the washing solution, FIG. 6 shows another embodiment of this invention, and FIG. 7 shows structural details of the sampling valve used in the embodiment shown in FIG. 6.

Referring to FIG. 1, a sample supply device 1 comprises a turntable 2 equipped with peripheral holes for accommodating a plurality of sample tubes 3, and a driving means 4 for rotating the turntable 2. A sampling head 5 comprises a suction tube 6 and a suction tube shifting device 7. By the action of the shifting device 7, the suction tube 6 is inserted into the sample tube containing the liquid sample next in line for examination. After sucking up the contents of the sample tube, the suction tube is automatically removed from the tube. Facilities for washing the inserted tip of the suction tube can be provided. In this case, the tube is inserted into a cleaning bath 8, as shown by the broken line, and sprayed with water, for example, from a nozzle 9. A sampling valve 10 comprises fixed members 11 and 12, and a rotatable member 13, said rotatable member 13 being arranged in close proximity between said fixed members 11 and 12. At least two passages 14a and 14b are provided having the same volume capacity as the rotatable member 13. The sampling valve 10 is in communication with a changeover valve 15, a pump 16 and a container 17. As will be seen from FIG. 1, a flow line runs from the sampling head 5 to the container 17 via the fixed member 11, the passage 14a, the fixed member 12, the changeover valve 15 and the pump 16. When the changeover valve 15 is positioned as shown by the solid line, the liquid sample contained in the sample tube 3 is sucked up through suction tube 6 through hole 14a. On the other hand, when the changeover valve 15 is positioned as shown by the broken line, the cleaning fluid 18 contained in the container 17 is sucked up and discharged in cleaning bath 8 via the sampling valve 10. By so doing, all traces of liquid sample adhering to the inner walls of the flow line removed. A rotatable reaction device 19 comprises a rotating member 20 which accommodates a plurality of reaction tubes 21 and a driving means (not shown in FIG. 1) which intermittently rotates the rotating member 20. The specific positions of the reaction tubes 21 are indicated on the drawing as A, B, C . . . L. A light source 22 is located at the center of the rotating member 20. A detector 23 subtends the light source 22. Two valves (not shown in FIG. 1) are provided at the upper and lower parts of the rotatable reaction device respectively.

Referring now to FIG. 2 which illustrates the rotatable reaction device in detail, upper 24 and lower 25 partitions enclose a volume maintained at a constant temperature, for example, 37° C. A pipe 26 is arranged so as to pass through said upper and lower partitions 24 and 25, said pipe 26 being fixed rigidly to said upper and lower partitions 24 and 25 by means of fixing members 27 and 28 and 29, respectively. A collar 30 is inserted and fixed to the pipe 26 and around the collar 30 a rotating member 20 is mounted on bearings 31 and 32. The rotating member 20 carries the reaction tubes 21 (in this particular embodiment 12 reaction tubes can be accommodated). The reaction tubes are made of a chemically resistant material such as quartz glass. Whatever the material, at least the portion through which light passes must be transparent. Passages 33 and 34 are provided for passing light and 35 is a reflecting mirror. Thus, a beam of light emitted from the light source 22 is reflected by reflecting mirror 35 so as to pass through passages 33 and 34 and irradiate reaction tubes 21. The transmitted light (i.e., the light which passes through the reaction tubes) is detected by a detector 23 housed in a shield case 36. A protection case housing 39 for the aforementioned light source 22 encloses a condenser lens 37 for converging the light emitted from light source 22 into a parallel beam, and a filter 38. A Geneva gear 40 is mounted on the upper face of the rotating member 20. The number of teeth on said gear is a multiple of the number of reaction tubes 21 (in this particular embodiment, the gear has 24 teeth). Eccentric plates 42 equipped with a pin 41 are connected to the shaft 43 which passes through and is supported by the upper partition 24. Pin 41 intermittently meshes with the Geneva gear 40. The upper part of the shaft 43 is equipped with a gear 43a, said gear 43a being linked to a motor or other such driving means 44 mounted on top of the partition 24. Accordingly, if the driving means 44 is made to operate in accordance with a predetermined program, pin 41 will rotate around the center of shaft 43. Since one complete rotation of the pin 41 turns the Geneva gear 40 from one tooth to the next, member 20 (complete with reaction tubes 21) is made to rotate intermittently. Valves 45 and 46 are provided at the upper and lower parts of the rotating member 20 respectively, said valves 45 and 46 comprising fixed blocks 47 and 49 and rotating blocks 48 and 50, respectively. Fixed block 47 is held by fixing member 27 and rotating block 48 is fixed to the upper part of the rotating member 20 via holder 51. On the other hand, fixed block 49 is secured to pipe 26 by holder 52 and rotating block 50 is fixed to the lower part of the rotating member 20 via holder 53. Passages 54 and 55 corresponding to the number of reaction tubes 21 are provided in said upper and lower valve rotating blocks 48 and 50, each set of passages being connected to the respective reaction tubes by pipes 56. On the other hand, passages 57 and 58 for feeding in and draining off the liquid samples, reagents, cleaning liquid, air, etc. are drilled through fixed blocks 47 and 49, each set of said passages being connected to a means for sucking up and exhausting the above mentioned liquids and gas via pipes 59 and 59'.

Referring once again to FIG. 1, position A of rotating member 20 (the first specified position) is the position where the liquid sample and first reagent are fed into the reaction tubes. It is also the position where lower valve 46 in FIG. 2, is connected to fixed member 12 forming part of the sampling valve 10. Fixed member 11, also forming part of the sampling valve 10, is connected by a pipe 61 to a preheating chamber 60 and a pump 62, the lower end of said pipe 61 extending beyond the pump 62 into a container 64 containing the first reagent 63.

FIG. 3 shows the composite structure of the reagent preheating chamber 60 in detail. The hermetically sealed chamber is filled with oil, water or air. The oil, etc. is heated by a heater 101 energized by a power source 100. A fan 103 is operated by a motor 102. The purpose of the fan is to keep the oil, etc. thoroughly mixed, thereby keeping its temperature uniform. A detector 104 is suitably located inside the preliminary heating chamber so as to monitor the temperature of the oil, etc. That is to say, the detector output signal is fed into a control circuit 105 which operates according to the strength of said output signal, thereby controlling the heater power source 100 so as to keep the temperature of the oil, etc. constant at approximately 37° C. The section of the pipe 61 inside the preheating chamber 60 is zigzag or spiral shaped, to prolong the passage of the first reagent and thereby allow it sufficient time to reach the aforementioned temperature of 37° C. For the same reason, the equivalent sections of pipes 65 and 66, which carry a second reagent and a cleaning fluid respectively, are similarly coiled.

Referring to FIG. 1, when pump 62 operates, the first reagent 63 is sucked up out of the container 64 and, after being heated to 37° C in the preheating chamber 60, proceeds along pipe 61 to the sampling valve 10. The liquid sample metered in the fixed capacity passage 14b of the rotating member 13 is ejected by said first reagent and the mixture is fed into the reaction tube located at position A of the rotating member 20 via lower valve 46 and pipe 59'.

FIG. 4 shows a means for stirring the mixture so as to accelerate the reaction process, said means being located midway between A and B. That is to say, when the reaction tube 21 reaches this position, upper valve 45 is connected to a vacuum pump 70 via pipes 59 and 68, and reservoir 69, and valve 46 is connected to resistance pipe 67 via pipe 59'. As a result, the air in the upper part of the reaction tube is drawn out through pipe 59, etc. and air (or any other suitable gas) is forced up through resistance pipe 67, etc. into the mixture contained in the reaction tube, thereby creating bubbles which serve to stimulate stirring.

When the reaction tube 21 reaches position H (see FIG. 1) lower valve 46 is connected to a pump 71 via pipes 59' and 65, the lower end of said pipe 65 extending beyond the pump 71 into a container 73 containing a second reagent 72. When pump 71 operates, the second reagent 72 is sucked up out of the container 73 and, after being heated to 37° C in the preheating chamber 60, proceeds along pipe 65 to the reaction tube 21 via lower valve 46. Another stirring means, identical to the one existing between positions A and B, is located between positions H and I. That is to say, when the reaction tube 21 reaches this position, air is supplied to said reaction tube via resistance pipe 74 and lower valve 46 (see FIG. 4). By so doing, the bubbles thus created stimulate the stirring of the second reagent and reacted sample (i.e., the mixture comprising the sample and first reagent).

Position J is the measuring position. That is to say, when the reaction tube reaches this position, the light from the light source 22 irradiates the contents of the reaction tube and is partially absorbed. The unabsorbed or transmitted light is detected by detector 23 and converted into an electrical signal, the output of which is amplified by an amplifier 75 prior to being fed into a recorder or display means 76. By so doing, the absorption coefficient of the light during the sample reaction process versus time can be recorded or displayed. Part of the amplified signal is digitalized in an A-D converter 77 prior to being sent to a data analyzer 78 for computation. The computed result, for example, the activated value of a specified enzyme can either be printed out each time a reaction tube reaches the J position or collectively, for a plurality of reaction tubes, as and when the information is required.

In connection with the measurement of absorbed light at the J position, a greater accuracy of measurement would be assured if compressed air is fed into the reaction tube via the upper end in order to compress the contents during the reaction process. By so doing, the large bubbles, so important for stimulating the stirring operation, are reduced in size to such an extent that they have little or no effect on the measuring accuracy. In this case, a pressure higher than that of the atmosphere (in the order of $2Kg/cm^2$, for example) is applied.

Positions K and L are the cleaning positions. At these positions, a cleaning liquid, e.g., water is pumped up through pipe 66 from a container 17 and, after passing through a pump 80, enters an air mixer 79. Air is sent to the air mixer 79 from a compressor 81 via a valve 82 in order to enhance the cleansing effect. The aerated mixture then proceeds through preheating chamber 60, lower valve 46 and pipe 59' prior to entering the reaction tube 21. The position midway between J and K is the position for draining the sample and reagent mixture, and the positions midway between K and L, and L and A are the positions for draining the cleaning solution 18 from the reaction tube. At these positions, compressed air from the compressor 81 enters the upper part of the reaction tube through pipe 84 via valve 83, pipes 59 and upper valve 45, and forces the measured sample and cleaning solution out of the reaction tube and into a receptacle (not shown) via drain pipe 85.

The complete operation of the above-described embodiment will now be described in conjunction with FIG. 5. Referring to the figure, (a) shows how the precise quantity of sample is measured out or metered. Liquid sample is drawn up from sample tube 3 by the action of pump 16 and measured out in sampling valve 10.

The next stage, as shown in (b) shows the sampling valve 10 positioned so that as the first reagent is drawn up out of container 64 by the action of pump 62, it mixes with the measured out sample and the mixture is carried to the reaction tube 21 which happens to be located at position A of the rotating member 20.

The rotating member 20 then makes a one-step rotation (i.e., 1/24th of a complete revolution) which brings the reaction tube containing the liquid sample and first reagent, to the stirring position as shown in (c). In this position, air is pumped out of the upper part of the reaction tube by the action of vacuum pump 70, thereby drawing in air from below via resistance pipe 67. As a result, the bubbles thus created enhance stirring of the liquid sample and first reagent.

FIG. 5(d) shows the reaction tube 21 positioned so that the second reagent is pumped out of container 73 by pump 71 and enters said reaction tube 21. That is to say, if the rotating member 20 is made to turn one or several steps, the reaction tube 21 will be positioned at the second reagent feed-in position. The time from when the first reagent and sample are fed into the reaction tube up to the time when the second reagent is fed into said tube is known as the prereaction time. It is during this time that the concentration of the first reagent is selected so as to coincide with the plateau domain or range of concentration in which the enzyme reaction rate remains unchanged.

The reaction tube 21 is then advanced one more step to the second stirring position as shown in (e). Here the procedure as described for (c) is repeated in order to improve the reaction uniformity.

Upon completion of stirring, the reaction tube is turned one or several steps to the J or measuring position as shown in (f). Here, light from light source 22 irradiates the transparent portion of the reaction tube for a fixed period of time, the transmitted portion of the light being detected by detector 23. The measuring time is in the order of several tens of seconds (e.g., 45 seconds) during which time, as the reaction progresses, the rate of decrease of the absorption coefficient is measured and the resultant signal is sent via amplifier 75 to a recorder and/or data analyzer. Thus, in the case of enzyme reaction, the activation value of the enzyme in question can be obtained. The program is set up so that the time during which the reaction tube stops at the respective positions (A, B, . . . L) is slightly longer than the measuring time, and the time during which the reaction tube stops at the positions midway between the A, B . . . L positions is about 10 seconds.

When measurement is complete, the reaction tube advances one more step to the position as shown by (g). Here, compressed air is fed into the upper part of the reaction tube via valve 83, thereby forcing the contents of the tube out through a drain pipe and into a receptacle.

This completed, the reaction tube advances to the cleaning position (FIG. 5(h). In this position, the cleaning solution in container 17 is drawn up by pump 80 and fed into the reaction tube. Simultaneously, compressed air passing through valve 82 is mixed with the cleaning solution to enhance the flushing process.

Finally, the aerated cleaning solution is drained (see (i)) using the same method as described in (g). Actually, in the embodiment described in FIG. 1, steps (h) and (i) are performed twice to ensure negligible cross-contamination. The reaction tube then returns to the original A position and the entire procedure from sampling to final drainage is repeated.

In the above-described embodiment, many liquid samples can be successively, rapidly, and accurately measured. Moreover, the activation values of the enzymes can be automatically and continuously obtained with high accuracy. Again, since the entire system of flow lines is of the "closed" type, reagent, cleaning solution, etc. is prevented from dispersing into the room during operation, thus keeping the place clean and safe.

The number of reagents used is not restricted to two as described in the embodiment according to FIG. 1. The use of one reagent is feasible or three, four, up to eight reagents may be used. In the latter case, however, positions B, C, D, E, F and G are used.

FIG. 6 shows another embodiment of this invention in which a plurality of analyses pertaining to the same sample can be carried out simultaneously. To make this possible, a plurality of rotatable reaction devices 19a, 19b . . . 19n are used, corresponding to which a plurality of preliminary heating chambers 60a, 60b, . . . 60n, pumps 62a, 62b, . . . 62n, 71a, 71b, . . . 71n and 80a, 80b, . . . 80n, reagent vessels 64a, 64b, . . . 64n and 73a, 73b, . . . 73n, detectors 23a, 23b, . . . 23n and amplifiers 75a, 75b, . . . 75n are provided. A separator 85 channels the compressed air produced by a compressor 81. A mixer 86 for mixing the cleaning solution with air and a joint 87 connect the plurality of rotatable reaction devices to the single vacuum pump 70.

FIG. 7 is a detailed illustration of the sampling valve used in the embodiment of FIG. 6. In the figure, the rotating member 13 is provided with passages 14a, 14b, . . . 14n having the same capacity and equidistant from the center axis of said rotating member 13. Passage 14a is connected to joint 88a which is fixed to fixed member 11, said joint 88a being connected to the sampling head 5 (see FIG. 6). Passage 14n is connected to joint 88b also fixed to fixed member 11, said joint 88b connected to pump 16 (see FIG. 6). 14a and 14b, 14b and 14c, . . . 14n-1 and 14n in fixed members 11 and 12 can be connected, in which case, when the sample in sample tube 3 is sucked up by pump 16, all the passages 14a, 14b, . . . 14n are filled with sample. Equally spaced joints 89a, 89b, 89c, . . . 89n and 90a, 90b, . . . 90n are fixed to fixed members 11 and 12 respectively, the small through holes (or channels) connected to said equally spaced joints extending to the lower and upper faces of the rotating member 13 respectively. Moreover, said small passages (or channels) are located on the same radial path as passages 14a, 14b . . . 14n.

By turning rotating member 13 slightly clockwise from the position indicated in FIG. 7, passages 14a, 14b . . . 14n are made to align with the aforementioned small passages (or channels). By so doing, if reagents are passed through joints 89a, 89b, . . . 89n, sample will be delivered to the reaction tubes via joints 90a, 90b, . . . 90n.

The above-described embodiments can be modified to suit specific requirements. For example, the sampling valve 10 is not limited to the type as heretofor described. Again, upper and lower valves 45 and 46 in FIG. 2 need not necessarily be built en bloc with the rotatable reaction device, and the light source 22 and detector could, if required, be positionally reversed.

Having described my invention with the detail and particularlity as required by the patent laws, what is desired protected by Letters Patent is set forth in the following claims:

1. An automatic analyzing apparatus comprising a rotatable reaction device in which a plurality of reaction tubes are circumferentially spaced, said reaction tubes having upper and lower ports, fixed upper and lower changeover valve blocks having passages that may be brought into registry with the upper and lower ports of said reaction tubes, means for irradiating reaction tubes and the contents thereof at at least one rotary position of the reaction device and means for detecting the amount of light passed through said reaction tube, whereby said reaction tubes may be connected sequentially to receive metered sample and reagents, to receive mixing gases, to exhaust the contents of said tubes and to receive abluents for cleaning said tubes as the rotatable reaction device is stepwise rotated.

2. An automatic analyzing apparatus as described in claim 1 in which the rotatable reaction device is arranged in an atmosphere maintained at a fixed temperature.

3. An automatic analyzing apparatus as described in claim 1 further comprising stirring means including a vacuum pump for evacuating the upper port of a reaction tube and a resistance pipe for allowing an inflow of suitable gas to the lower port to stimulate stirring.

4. An automatic analyzing apparatus as described in claim 1 further comprising means for preheating a reagent to a specific temperature.

5. An automatic analyzing apparatus as described in claim 1 further comprising means for preheating the abluent for washing the reaction tubes to a specific temperature.

6. An automatic analyzing apparatus as described in claim 1 further comprising means for mixing air with an abluent used for washing the reaction tubes.

7. An automatic analyzing apparatus as described in claim 1 further comprising means for performing the washing operation at least twice.

8. An automatic analyzing apparatus as described in claim 1 further comprising means for pressurizing by compressed air the upper part of the reaction tube when light detection measurement is being carried out.

9. An automatic analyzing apparatus comprising a rotatable reaction device in which a plurality of reaction tubes are circumferentially spaced, said reaction tubes having upper and lower ports, upper and lower changeover valves comprising a fixed portion and a rotating portion arranged to rotate with said reaction device, said rotating portions of the upper and lower changeover valves having passages that respectively communicate with the upper and lower ports of said reaction tubes, whereby said upper and lower valves sequentially introduce metered sample and reagents to said tubes, introduce mixing gases to said tubes, exhaust the contents of said tubes and introduce abluents for cleaning said tubes as the rotatable reaction device and rotatable portions of the upper and lower valves are stepwise rotated.

* * * * *